US011197699B2

(12) United States Patent
Prien et al.

(10) Patent No.: US 11,197,699 B2
(45) Date of Patent: Dec. 14, 2021

(54) IMPLANT SYSTEM FOR BONE FIXATION

(71) Applicant: Stryker European Operations Holdings LLC, Kalamazoo, MI (US)

(72) Inventors: Ole Prien, Kiel (DE); Matthias Rump, Schoenkirchen (DE); Hendrik Kluever, Schoenkirchen (DE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 0 days.

(21) Appl. No.: 17/220,432

(22) Filed: Apr. 1, 2021

(65) Prior Publication Data
US 2021/0220026 A1 Jul. 22, 2021

Related U.S. Application Data

(63) Continuation of application No. 15/574,720, filed as application No. PCT/US2015/032241 on May 22, 2015.

(51) Int. Cl.
| | | |
|---|---|---|
| *A61B 17/72* | (2006.01) | |
| *A61B 17/74* | (2006.01) | |
| *A61B 17/88* | (2006.01) | |

(52) U.S. Cl.
CPC .......... *A61B 17/7241* (2013.01); *A61B 17/72* (2013.01); *A61B 17/744* (2013.01); *A61B 17/8897* (2013.01)

(58) Field of Classification Search
CPC .......... A61B 17/72–748; A61B 17/844; A61B 17/846; A61B 17/848; A61B 17/86
See application file for complete search history.

(56) References Cited

U.S. PATENT DOCUMENTS 4,875,475 A * 10/1989 Comte ............... A61B 17/7225
606/64
5,176,681 A * 1/1993 Lawes .................. A61B 17/744
606/64
(Continued)

FOREIGN PATENT DOCUMENTS

EP        2253285 A1   11/2010
WO   2012099944 A1    7/2012
(Continued)

OTHER PUBLICATIONS

Extended European Search Report including the Written Opinion for Application No. 19182207.1 dated Oct. 25, 2019, 8 pages.
(Continued)

*Primary Examiner* — Lynnsy M Summitt
(74) *Attorney, Agent, or Firm* — Lerner, David, Littenberg, Krumholz & Mentlik, LLP

(57) ABSTRACT

An implant system for use in orthopaedic surgery for fixation of bone includes an intramedullary nail and a coupling member. The intramedullary nail includes a proximal portion defining a longitudinal axis. The proximal portion includes an axial bore defining an axis substantially parallel to the longitudinal axis of the proximal portion and a transverse bore configured to receive a bone fastener. The coupling member includes a through hole and is movably arranged within the axial bore of the proximal portion. Further, the coupling member includes a drive portion and a bone fastener engagement portion. The drive portion is in one variant non-rotatably coupled to the bone fastener engagement portion. The bone fastener engagement portion is configured to engage the bone fastener penetrating the transverse bore. In one variant the engagement is realized via an extended contact region.

19 Claims, 6 Drawing Sheets

(56) References Cited

U.S. PATENT DOCUMENTS

| | | |
|---|---|---|
| 6,123,708 A | 9/2000 | Kilpela et al. |
| 6,235,031 B1 | 5/2001 | Hodgeman et al. |
| 6,406,477 B1 | 6/2002 | Fujiwara |
| 6,443,954 B1 | 9/2002 | Bramlet et al. |
| 6,921,400 B2 | 7/2005 | Sohngen |
| 7,771,428 B2 | 8/2010 | Siravo et al. |
| 8,114,079 B2 | 2/2012 | Haidukewych et al. |
| 8,568,414 B2 | 10/2013 | Siravo et al. |
| 8,790,343 B2 | 7/2014 | McClellan et al. |
| 8,808,293 B2 | 8/2014 | Buettler et al. |
| 8,840,675 B2 | 9/2014 | Song |
| 8,906,023 B2 | 12/2014 | Matityahu et al. |
| 9,072,552 B2 | 7/2015 | Simon et al. |
| 9,198,701 B2 | 12/2015 | Prien et al. |
| 9,220,544 B2 | 12/2015 | Matityahu et al. |
| 9,282,975 B2 | 3/2016 | Sweeney |
| 9,295,504 B2 | 3/2016 | Haidukewych et al. |
| 9,433,448 B2 | 9/2016 | Ehmke et al. |
| 9,433,449 B2 | 9/2016 | Vega et al. |
| 9,526,542 B2 | 12/2016 | Ehmke |
| 9,782,206 B2 | 10/2017 | Mueckter et al. |
| 9,814,499 B2 | 11/2017 | Buscaglia et al. |
| 9,936,989 B2 | 4/2018 | Halder |
| 10,080,596 B2 | 9/2018 | Ehmke |
| 10,123,828 B2 | 11/2018 | Matityahu et al. |
| 2003/0074000 A1 | 4/2003 | Roth et al. |
| 2005/0203510 A1 | 9/2005 | Sohngen |
| 2006/0200160 A1 | 9/2006 | Border et al. |
| 2007/0233102 A1 | 10/2007 | Metzinger |
| 2008/0249580 A1 | 10/2008 | Evans et al. |
| 2010/0249781 A1 | 9/2010 | Haidukewych et al. |
| 2011/0196372 A1 | 8/2011 | Murase |
| 2014/0088595 A1* | 3/2014 | Mueckter ............ A61B 17/744 606/64 |
| 2015/0157369 A1* | 6/2015 | Ehmke ............... A61B 17/7241 606/64 |
| 2018/0116747 A1 | 5/2018 | Matityahu et al. |

FOREIGN PATENT DOCUMENTS

| | | |
|---|---|---|
| WO | 2012107056 A1 | 8/2012 |
| WO | 2015059717 A1 | 4/2015 |

OTHER PUBLICATIONS

International Search Report for Appln. No. PCT/US2015/032241 dated Nov. 17, 2015, 4 pages.

* cited by examiner

IMPLANT SYSTEM FOR BONE FIXATION

CROSS-REFERENCE TO RELATED APPLICATIONS

The present application is a continuation application claiming priority to U.S. patent application Ser. No. 15/574,720, which is a national phase entry under 35 U.S.C. § 371 of International Application No. PCT/US2015/032241 filed May 22, 2015, the disclosure of which is incorporated herein by reference.

TECHNICAL FIELD

The present disclosure generally relates to an implant system for use in orthopaedic surgery. Specifically, the disclosure relates to an intramedullary nail for internal fixation of bone, such as a femur.

BACKGROUND OF THE INVENTION

Femur fractures commonly occur in the femoral neck and the trochanteric regions. Typically, trochanteric and subtrochanteric femur fractures are currently treated with an intramedullary nail having a transverse bore to receive a bone fastener, such as a femoral neck screw usually provided in the form of a lag screw. The intramedullary nail is fitted in the intramedullary canal of the femur and the lag screw passes through the transverse bore of the intramedullary nail, through the neck of the femur and into the femoral head.

The lag screw is designed to transfer the load of the femoral head into the nail shaft by bridging the fracture line to allow fast and secure fracture healing. Further, the lag screw is allowed to slide in the intramedullary nail in accordance with the sintering of the femoral fracture. Typically, a set screw is inserted into a bore of the intramedullary nail to prevent a rotation and an uncontrolled medial deviation of the lag screw.

The intramedullary nail may include a central cannulation along its longitudinal axis for receiving a surgical wire (guide wire), such as a Kirschner-wire. The surgical wire is inserted into the marrow cavity of the femur prior to the insertion of the intramedullary nail.

U.S. Pat. Pub. No. 2010/0249781 relates to an intramedullary nail assembly having a lag screw lock positioned within the hollow upper portion of the intramedullary shaft. The lag screw lock includes a main body portion and a threaded head portion that is rotatably connected to the main body portion. A lower rim portion is formed around the opening at the bottom of the main body portion, with the rim defining a locking surface to engage a lag screw.

U.S. Pat. Pub. No. 2005/0203510 relates to a fixation instrument for treating a femoral neck or intratrochanteric fracture. The fixation instrument includes a nail member and an insert which is disposed within a chamber located in the proximal end of the nail member. The insert has a lower surface with a pair of locking projections extending longitudinally downward from the lower surface. The locking projections can engage a bone screw disposed in an aperture of the nail member. A threaded locking ring threadably engages a thread disposed on the sidewalls of the chamber of the nail member. The locking ring is attached to the insert by a snap fit to rotatably secure the locking ring to the insert, such that the locking ring can rotate about the longitudinal axis of the insert while the insert is prevented from rotating in the chamber.

The conventional intramedullary nails and set screws have several drawbacks. A set screw having a main body engagement portion and a threaded head drive portion rotatably connected thereto cannot be easily preassembled within the intramedullary nail. Further, the conventional set screws need a guiding structure within the proximal portion of the intramedullary nail for guiding their bone engagement portions (e.g., pins or prongs). Such a complicated two-piece structure of the set screw allows potential risks of getting stuck or jammed during preassembling into the axial bore of the proximal portion of the intramedullary nail and during sliding of the set screw within the intramedullary nail toward the lag screw penetrating the intramedullary nail. Thus, the insertion of the relatively small set screw into the shaft of the intramedullary nail is cumbersome and the operation time increases due to additional operation steps. Moreover, a set screw having one or more prongs or rims cannot prevent an uncontrolled medial deviation of the lag screw. Hence, the construct of intramedullary nail, set screw and lag screw inserted through the transverse bore of the intramedullary nail and into bone can therefore not provide a high mechanical load stability within the body of the patient.

BRIEF SUMMARY OF THE INVENTION

Aspects of the present disclosure are directed to providing an implant system simplifying and facilitating the surgical procedure and implantation of an intramedullary nail and corresponding bone fasteners, as well as providing a sufficient mechanical load construct stability within the body of a patient.

According to a first aspect, there is provided an implant system for use in orthopaedic surgery for fixation of bone. The implant system comprises an intramedullary nail with a proximal portion defining a longitudinal axis. The proximal portion includes an axial bore defining an axis substantially parallel to the longitudinal axis of the proximal portion and a transverse bore configured to receive a bone fastener. Further, the implant system comprises a coupling member with a through hole and configured to be movably arranged within the axial bore of the proximal portion of the intramedullary nail. The coupling member includes a drive portion and a bone fastener engagement portion. The drive portion is non-rotatably coupled to the bone fastener engagement portion. The bone fastener engagement portion is configured to engage the bone fastener penetrating the transverse bore.

The drive portion and the bone fastener engagement portion may be formed in one piece. Thus, in one implementation, the drive portion and the bone fastener engagement portion may constitute a one-piece structure. The bone fastener engagement portion can be rigidly coupled to the drive portion.

In one realization, the bone fastener engagement portion may define an outer diameter which is smaller than an outer diameter of the drive portion. The outer diameters can lie within a plane which is substantially perpendicular to an axis of the through hole of the coupling member.

The bone fastener engagement portion may include a rounded (e.g., partially circular or oblong) edge at its end facing the transverse bore. The rounded edge may extend along the outer circumference of the bone fastener engagement portion. Further, the rounded edge of the bone fastener engagement portion may be configured to engage the bone fastener penetrating the transverse bore. In one aspect, the rounded edge of the bone fastener engagement member can be configured to engage within a groove of the bone fastener. A part of the rounded edge of the bone fastener engagement portion may be configured to engage within a groove of the bone fastener in an eccentric fashion. In such a case, a part of the rounded edge can engage within a groove of the bone fastener at a medial or lateral side of the intramedullary nail.

The bone fastener engagement portion may have an extended (e.g., elongated or otherwise non-point shaped) contact region configured to engage the bone fastener (e.g., within the groove thereof). The contact region can have the shape of a curved or non-curved line, or may have a two-dimensional extension (i.e., it may take the form of a contact surface). In one aspect, the rounded edge of the bone fastener engagement portion may define a rounded contact region configured to engage a complementary shaped contact region of the bone fastener. The bone fastener engagement portion can define an arc segment in cross section. The rounded edge of the bone fastener engagement portion and a groove of the bone fastener can substantially define complementary arc segments in cross-section.

The coupling member may be configured to urge, upon moving of the drive portion toward a distal portion of the intramedullary nail, the bone fastener engagement portion in the direction of the longitudinal axis of the proximal portion towards the distal portion. In such a case the bone fastener engagement portion may engage within a groove or any other structure of the bone fastener to prevent rotation of the bone fastener about a longitudinal axis of the bone fastener.

The coupling member may define a plane at its end face pointing in a distal direction of the intramedullary nail, wherein the plane is substantially perpendicular to the longitudinal axis of the proximal portion of the intramedullary nail. Further, the coupling member may be formed as a (short) bolt.

In one realization, the drive portion and the bone fastener engagement portion can be penetrated by the though hole of the coupling member. Thus, the drive portion and/or the bone fastener engagement portion may include a through hole for receiving a surgical wire. Further, the through hole of the coupling member, of the drive portion and/or of the bone fastener engagement portion may be arranged centrally or eccentrically. The through hole of the coupling member may define an axis substantially parallel to the axis of the axial bore of the proximal portion of the intramedullary nail.

The intramedullary nail may include a channel substantially along a longitudinal axis of the intramedullary nail. The channel of the nail may have a circular or angular shape in cross-section. A cannulation can be defined through the intramedullary nail by the channel of the intramedullary nail, the through hole of the coupling member and the axial bore of the proximal portion, such that a surgical wire may be inserted through the cannulation. The surgical wire may be a guide wire, such as a Kirschner-wire or any other kind of wire.

In one implementation, the drive portion of the coupling member may have an external thread for threadable engagement with the intramedullary nail, for example with the proximal portion of the intramedullary nail. The axial bore of the proximal portion of the intramedullary nail may include an internal thread, wherein the external thread of the drive portion of the coupling member can be configured to mate with the internal thread of the axial bore of the proximal portion of the intramedullary nail.

The implant system may further comprise the bone fastener. The bone fastener can be formed as a sliding screw, a lag screw or femoral neck screw or any kind of blade. The bone fastener may comprise one or more grooves or other structures. The one or more grooves or other structures may have one or more ramps for engagement by the bone fastener engagement portion of the coupling member. Each ramp of the at least one groove or other structure can have a shallow end and a deeper end. The rising ramp may extend from the shallow end at a rear end of the bone fastener towards a front end of the bone fastener to the deeper end. In one implementation, the at least one groove or other structure may have a width at the deeper end greater than a width at the shallow end. The bone fastener engagement portion of the coupling member may be configured to engage within the one or more grooves or other structures of the bone fastener to prevent rotation of the bone fastener about a longitudinal axis of the bone fastener.

The coupling member may be captively held within the proximal portion (e.g., within the axial bore) of the intramedullary nail. Moreover, the coupling member may be preassembled within the proximal portion (e.g., within the axial bore) of the intramedullary nail.

Also provided is an intramedullary nail for use in orthopaedic surgery for fixation of bone, comprising a proximal portion defining a longitudinal axis, wherein the proximal portion includes an axial bore defining an axis substantially parallel to the longitudinal axis of the proximal portion and a transverse bore configured to receive a bone fastener, and a coupling member with a through hole captively held and movably arranged within the axial bore of the proximal portion of the intramedullary nail, the coupling member including a drive portion and a bone fastener engagement portion, wherein the drive portion is non-rotatably coupled to the bone fastener engagement portion, and wherein the bone fastener engagement portion is configured to engage a bone fastener penetrating the transverse bore.

According to a further aspect there is provided an implant system for use in orthopaedic surgery for fixation of bone, comprising an intramedullary nail with a proximal portion defining a longitudinal axis, wherein the proximal portion includes an axial bore defining an axis substantially parallel to the longitudinal axis of the proximal portion and a transverse bore configured to receive a bone fastener, and a coupling member with a through hole and configured to be movably arranged within the axial bore of the proximal portion of the intramedullary nail, the coupling member including a drive portion and a bone fastener engagement portion, wherein the bone fastener engagement portion includes an extended contact region configured to engage a complementary shaped contact region of a bone fastener penetrating the transverse bore. The implant system may be further configured as generally described above or hereinafter.

According to a further aspect there is provided a method of fracture fixation of bone, the method comprising the steps of inserting a guide wire into a marrow cavity of bone; inserting a cannulated intramedullary nail over the guide wire into the marrow cavity of bone, wherein the intramedullary nail comprises a proximal portion defining a longitudinal axis, wherein the proximal portion includes an axial bore defining an axis substantially parallel to the longitudinal axis of the proximal portion and a transverse bore configured to receive a bone fastener, and a coupling member with a through hole movably arranged within the axial bore of the proximal portion of the intramedullary nail, the coupling member including a drive portion and a bone fastener engagement portion, wherein (i) the drive portion is non-rotatably coupled to the bone fastener engagement portion and/or (ii) wherein the bone fastener engagement portion includes an extended contact region configured to engage a bone fastener penetrating the transverse bone; removing the guide wire; inserting a bone fastener through the transverse bore of the intramedullary nail into bone for stabilization of the bone fracture; and driving the coupling member for producing an engagement of the bone fastener engagement portion with the bone fastener penetrating the transverse bore of the intramedullary nail, thereby preventing rotation of the bone fastener. In variant ii), the engagement occurs via the extended contact region.

When the coupling member, for example, in form of a set screw, includes a bone fastener engagement portion and a drive portion with a through hole, the coupling member (i.e., the drive portion non-rotatably coupled to the bone fastener engagement portion) can easily be preassembled or preloaded within the intramedullary nail, while allowing simultaneous passage of a surgical wire. In particular, the surgical procedure and the implantation of the intramedullary nail within an intramedullary canal of a femur is simplified and facilitated. Further, due to the one-piece structure of the coupling member, the potential risks of getting stuck or jammed during preassembling into the axial bore of the proximal portion of the intramedullary nail and during sliding of the coupling member within the intramedullary nail toward the bone fastener is significally reduced. Moreover, a specific guiding structure for guiding the bone fastener engagement portion of the set screw within the axial bore of the proximal portion of the intramedullary nail is not necessary.

BRIEF DESCRIPTION OF THE DRAWINGS

These and other features, aspects and advantages of the present disclosure will become more apparent from the following detailed description taken in conjunction with the accompanying drawings, wherein.

DETAILED DESCRIPTION

Figure 1:
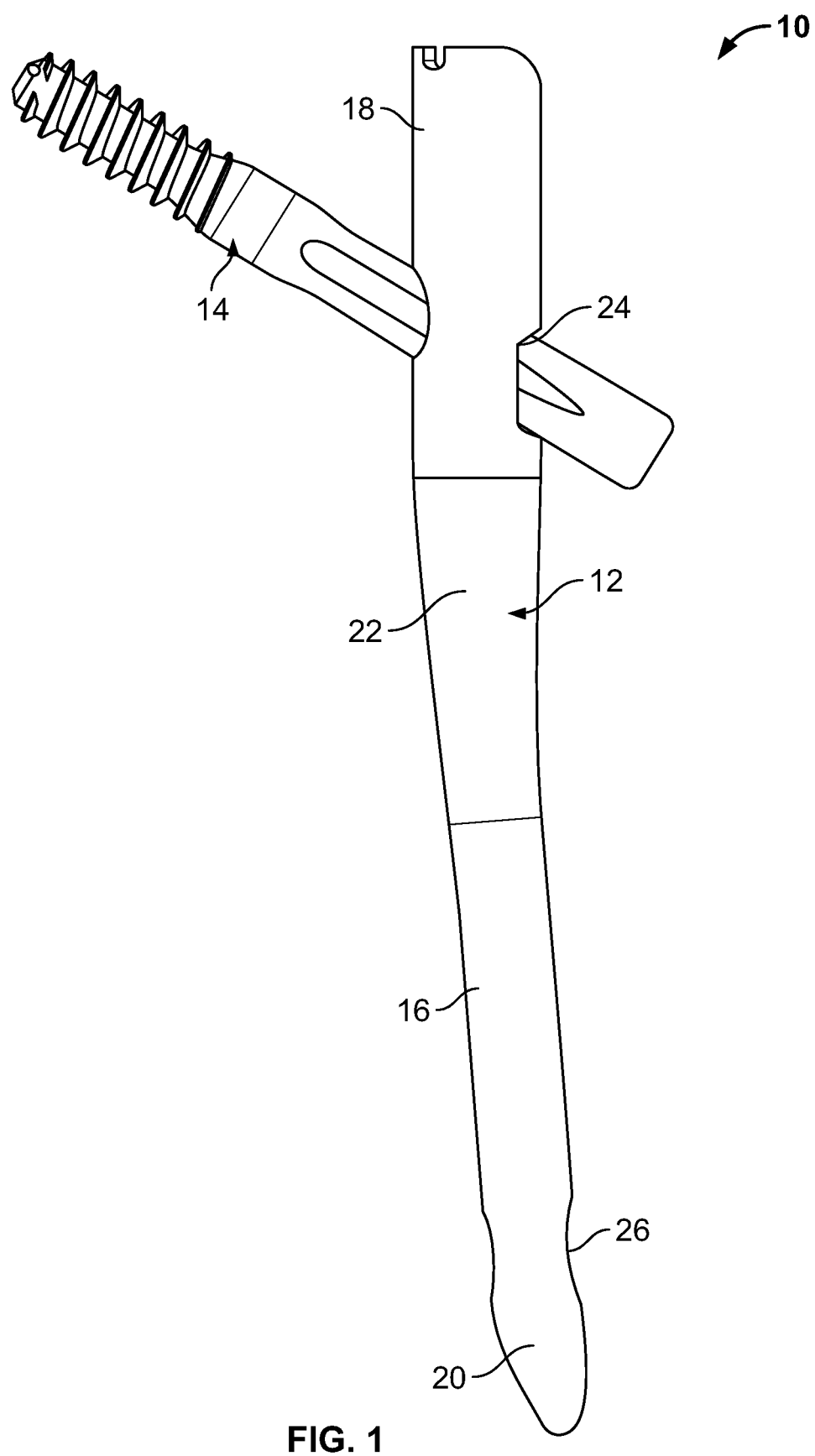
FIG. 1 is a side view of an implant system embodiment.

In the following description of exemplary embodiments, the same or similar components will be denoted by identical reference numerals. It will be appreciated that certain components of different configurations may interchangeably be provided in different embodiments. It will further be appreciated that while the following embodiments will primarily be described with respect to the treatment of a femur, the implant system presented herein can also be used for other treatments.

Referring to FIG. 1, there is shown a side view of an embodiment of an implant system 10 for use in orthopaedic surgery for fixation of bone, such as a femur (not shown in FIG. 1). The implant system 10 comprises an intramedullary nail 12 and a bone fastener 14. The intramedullary nail 12 includes a rod-shaped body 16 insertable into the inner cavity (marrow cavity) of the femur, i.e., into the intramedullary canal of the femur. The rod-shaped body 16 of the intramedullary nail 12 includes a proximal portion 18, a distal portion 20 which is longer than the proximal portion 18, and a bent portion 22 located between the proximal portion 18 and the distal portion 20. In other words, the bent portion 22 connects the proximal portion 18 and the distal portion 20.

Figure 2:
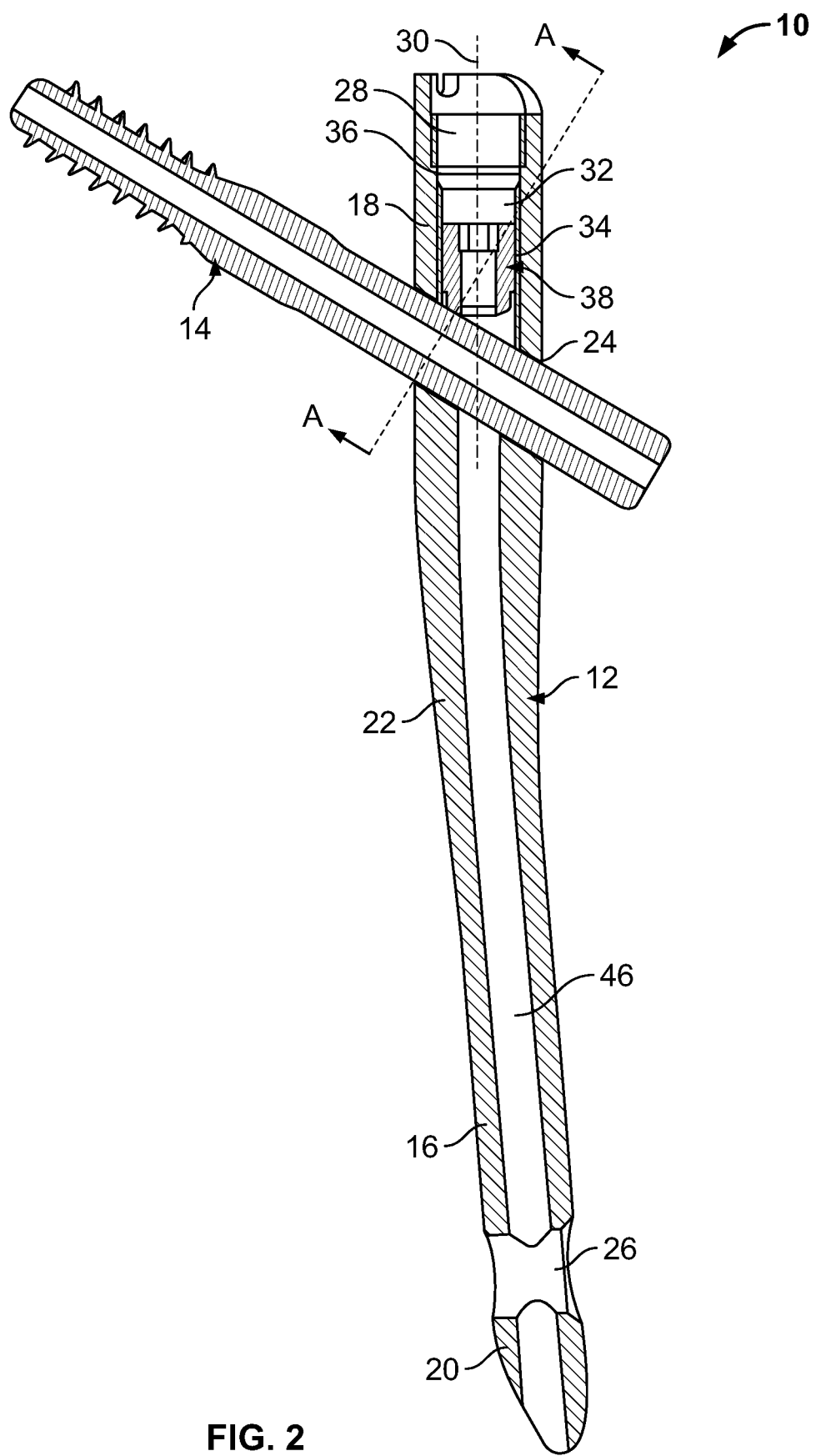
FIG. 2 is a cross-sectional view of the implant system embodiment shown in FIG. 1.

FIG. 2 illustrates a cross-sectional view of the implant system embodiment 10 shown in FIG. 1. As shown in FIG. 2, the intramedullary nail 12 includes a transverse bore 24 located at the proximal portion 18. An axis of the transverse bore 24 has an angle with respect to a longitudinal axis of the intramedullary nail 12, such that a longitudinal axis of the transverse bore 24 has an oblique extension relative to an axial extension of the proximal portion 18. While in the present embodiment only a single transverse bore 24 is utilized, in other embodiments multiple (e.g., two or more) transverse bores may be provided in the proximal portion 18.

In the embodiment of the implant system 10 shown in FIG. 2, the bone fastener 14 is a femoral neck screw in the form of a lag screw 14. The lag screw 14 is adapted to penetrate the transverse bore 24 of the intramedullary nail 12.

The proximal portion 18 of the intramedullary nail 12 has a diameter sufficient to accommodate the transverse bore 24 therein, while the distal portion 20 of the intramedullary nail 12 has a smaller diameter with respect to the proximal portion 18, adapted to the shape of the marrow cavity of the femur in order to facilitate the insertion of the distal portion 20 into the intramedullary canal. Further, the distal portion 20 includes a through hole 26 extending substantially orthogonally to a longitudinal axis of the distal portion 22. The through hole 26 is formed at an end of the distal portion 22 of the intramedullary nail 12 for receiving a bone fastener, such as a locking screw, in order to securely fix the intramedullary nail 12 to bone.

As illustrated in FIG. 2, the proximal portion 18 of the intramedullary nail 12 includes a recess 28 for receiving an end cap or a tool, such as a holding instrument or targeting instrument (not shown in FIG. 2) at the upper end of the proximal portion 18. The proximal portion 18 defines a longitudinal axis 30 and further includes an axial bore 32. The axial bore 32 defines an axis which is substantially parallel to the longitudinal axis 30 of the proximal portion 18. In the present embodiment, the axial bore 32 of the proximal portion 18 is co-axial with the longitudinal axis 30 of the proximal portion 18. As further shown in FIG. 2, the axial bore 32 includes an internal thread 34 and a recess portion 36 for receiving a retainer exemplary in form of a snap ring (not shown in FIG. 2).

The implant system 10 further comprises a coupling member 38. The coupling member 38 couples the lag screw 14 to the intramedullary nail 12. The coupling member 38 will be explained in more detail with reference to FIG. 3.

Figure 3:
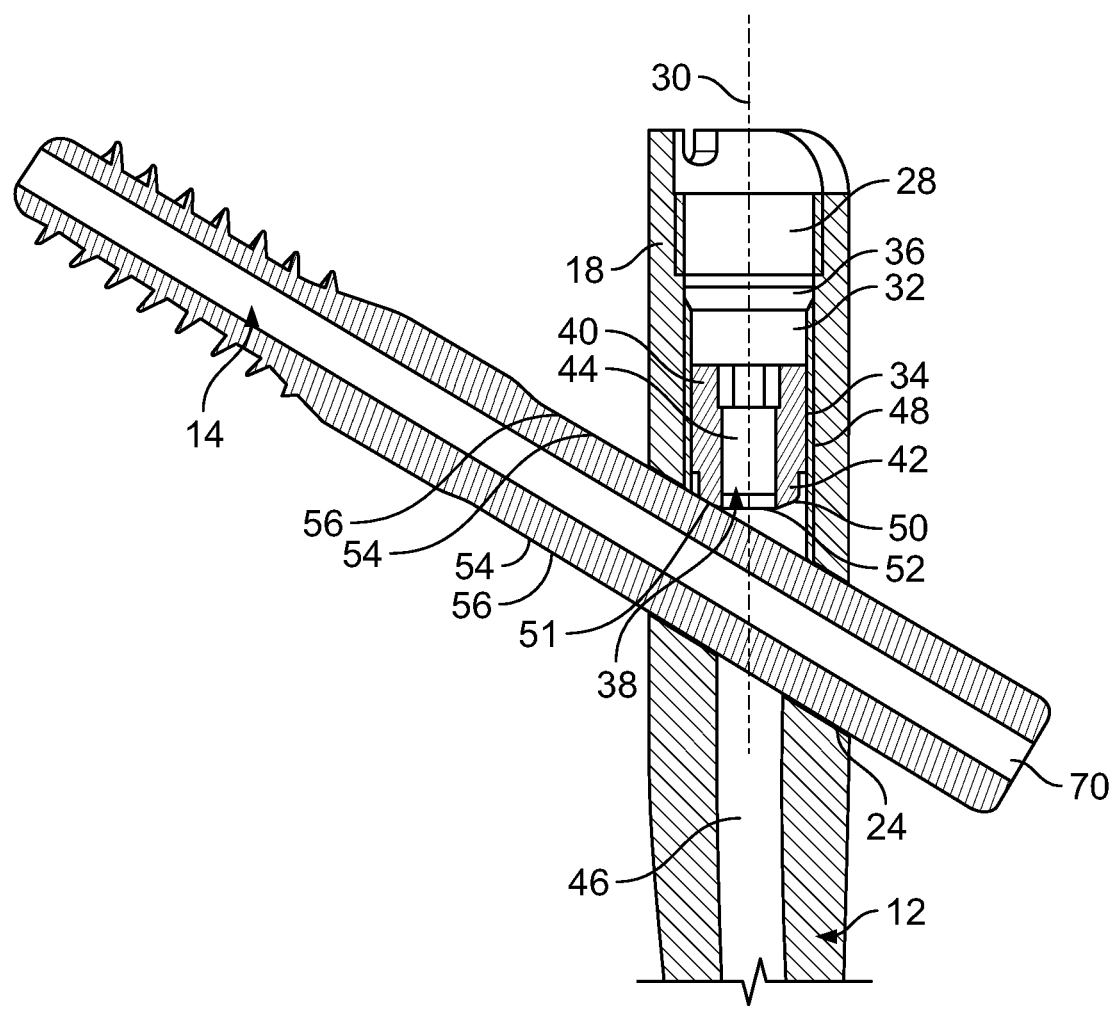
FIG. 3 is a detailed cross-sectional side view of a proximal portion of the implant system embodiment shown in FIG. 2.

FIG. 3 illustrates a detailed view in cross-section of the proximal portion 18 of the implant system embodiment 10 shown in FIGS. 1 and 2. The coupling member 38 is preassembled and movably arranged within the axial bore 32 of the proximal portion 18 of the intramedullary nail 12. As shown in FIG. 3, the coupling member 38 is captively held within the proximal portion 18 of the intramedullary nail 12. The coupling member 38 includes a drive portion 40 and a bone fastener engagement portion 42. The drive portion 40 is non-rotatably coupled to the bone fastener engagement portion 42. In the present embodiment, the drive portion 40 and the bone fastener engagement portion 42 are formed in one piece (i.e., the coupling member 38 constitutes a one-piece structure).

As shown in FIG. 3, the coupling member 38 includes a through hole 44. The drive portion 40 and the bone fastener engagement portion 42 are penetrated by the through hole 44 of the coupling member 38. The through hole 44 of the coupling member defines an axis substantially parallel to the axis of the axial bore 32 of the proximal portion 18 of the intramedullary nail 12. In the present embodiment as shown in FIGS. 2 and 3, the through hole 44 of the coupling member 44 is a central through hole having an axis which coincides with the longitudinal axis 30 of the proximal portion 18.

The intramedullary nail 12 further includes a channel 46 substantially along the longitudinal axis of the intramedullary nail 12. Thus, a cannulation is defined through the intramedullary nail 12 by the channel 46 of the intramedullary nail 12, the through hole 44 of the coupling member 38 and the axial bore 32 of the proximal portion 18, such that a surgical wire (not shown in FIGS. 2 and 3) can be inserted through the cannulation.

As further shown in FIGS. 2 and 3, the drive portion 40 of the coupling member 38 includes an external thread 48 on its outer peripheral surface for threadable engagement with the intramedullary nail 12 (e.g., with the proximal portion 18 as illustrated in FIGS. 2 and 3). The internal thread 34 of the axial bore 32 of the proximal portion 18 mates with the external thread 48 of the drive portion 40 of the coupling member 38.

The bone fastener engagement portion 42 is configured to engage the lag screw 14 penetrating the transverse bore 24. In the present embodiment, the bone fastener engagement portion 42 includes a rounded edge 50 at its end 52 facing the transverse bore 24. The rounded edge 50 can engage within a groove 54 of the lag screw 14.

Upon moving of the coupling member 38 towards the distal portion 20 of the intramedullary nail 12, the coupling member 38 (particularly, the drive portion 40 of the coupling member 38) urges the bone fastener engagement portion 42 in the direction of the longitudinal axis 30 of the proximal portion 18 towards the distal portion 20 of the intramedullary nail 12. The coupling member 38 thus slides within the axial bore 32 of the proximal portion 18 towards the lag screw 14. In a final position (as shown in FIG. 3), the rounded edge 50 of the bone fastener engagement portion 42 engages within one of the grooves 54 of the lag screw 14 to prevent rotation of the lag screw 14 about its longitudinal axis.

As illustrated in FIGS. 2 and 3, a part of the rounded edge 50 of the bone fastener engagement portion 42 engages within the groove 54 of the lag screw 14 in an eccentric fashion, i.e., in an eccentric position (e.g., at a medial position as shown FIG. 3). Upon engagement within the groove 54, the bone fastener engagement portion 42 can exert pressure on the lag screw 14 for stabilization purposes. The pressure is initially zero or low enough to still permit a sliding movement of the lag screw 14 relative to the intramedullary nail 12. The pressure will change (and typically increase) as the lag screw 14 slides due to the depth profile (i.e., laterally and medially provided ramps 56) of the grooves 54.

The eccentric engagement of the bone fastener engagement portion 42 of the coupling member 38 thus allows an engagement within a groove 54 of the lag screw 14. The cannulation formed by the canal 46 of the intramedullary nail 12, the central through hole 44 of the coupling member 38 and the axial bore 32 of the proximal portion 18 allows the simultaneous inserting of a guide wire.

The range of motion (i.e., the movement) of the coupling member 38 in the proximal direction can be limited by the retainer (not shown). The retainer may be formed as a snap ring or spring ring having a defined spring constant and may engage within the recess portion 36. The retainer can further have a circular shape. The recess portion 36 is formed as a circumferential groove within the proximal portion 18 of the intramedullary nail 12 to avoid an unintended disassembling of the coupling member 38.

Figure 4:
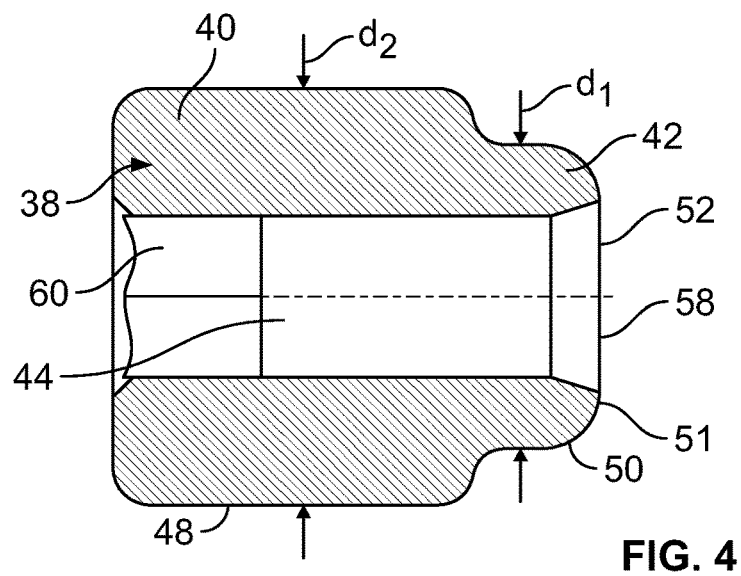
FIG. 4 is a cross-sectional side view of a coupling member embodiment.

Referring to FIG. 4, there is shown a cross-sectional side view of the coupling member embodiment 38 as used with the implant system embodiment 20 shown in FIGS. 1 to 3. The coupling member 38 defines a plane 58 at its end face pointing in a distal direction of the intramedullary nail 12. As shown in FIGS. 2 and 3, the plane 58 is substantially perpendicular to the longitudinal axis 30 of the proximal portion 18 of the intramedullary nail 12. Further, the bone fastener engagement portion 42 defines an outer diameter d1 which is smaller than an outer diameter d2 of the drive portion 40. The outer diameters d1 and d2 lie within a plane which is substantially perpendicular to an axis of the through hole 44 of the coupling member 38. Thus, a circumferential step is defined by the drive portion 40 and the bone fastener engagement portion 42.

As further shown in FIG. 4, the bone fastener engagement portion 42 is rigidly coupled to the drive portion 40, i.e. the coupling member is integrally formed (e.g., formed from one piece). In the present embodiment, the coupling member 32 is formed as a short bolt.

The drive portion 40 of the coupling member 38 has a receiving portion 60 in form of a cone having a recess (e.g., in the form of a hexalobular internal driving feature or internal hexagon) for receiving a tool, screwdriver, wrench or the like. By driving the drive portion 40 using such a tool, the entire coupling member 38 moves along the longitudinal axis 30 of the proximal portion 18 of the intramedullary nail 12, since the external thread 48 of the drive portion 40 mates with the internal thread 34 of the axial bore 32 of the proximal portion 18. In other words, the position of the coupling member 38 within the proximal portion 18 of the intramedullary nail 12 can be adjusted by screwing the drive portion 40 of the coupling member 32 along the longitudinal axis 30.

Figure 5:
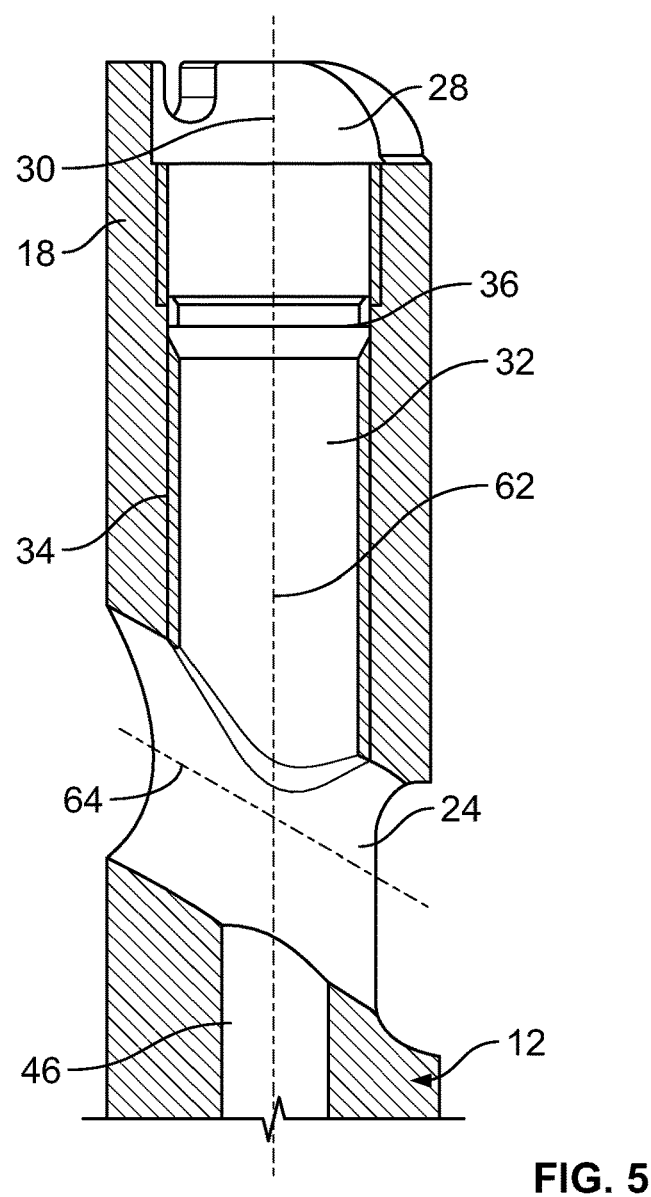
FIG. 5 is a detailed cross-sectional view of the proximal portion of the implant system embodiment shown in FIG. 2.

FIG. 5 illustrates a detailed cross-sectional view of the proximal portion 18 of the intramedullary nail 12 of the implant system embodiment 10 shown in FIGS. 1 to 3 (the coupling member 38 is not shown in FIG. 5). As shown in FIG. 5, the axial bore 32 of the proximal portion 18 defines an axis 62 which, in the present embodiment, coincides with the longitudinal axis 30 of the proximal portion 18. In other embodiments, the axis 62 of the axial bore 32 may be spaced apart from and extend parallel to the longitudinal axis 30 of the proximal portion 18. In certain cases, the axis 62 of the axial bore 32 may be slightly inclined (e.g., at an angle of up to 10° or 15°) with respect to the longitudinal axis 30 of the proximal portion 18 and thus remain at least substantially parallel thereto. Further, the axial bore 32 of the proximal portion 18 may be located at the medial side or at the lateral side of the intramedullary nail 12 or is centrally located with respect to the longitudinal axis 30 of the proximal portion 18.

The terms medial and lateral are standard anatomical terms of direction and denote a direction toward the center or median plane of a body and the opposite direction from the center to the side, respectively. With respect to the overall present disclosure and the exemplary embodiments, the medial and lateral directions may generally lie within a plane including the longitudinal axis 30 of the proximal portion 18 and a longitudinal axis 64 of the transverse bore 24. In such a case, the medial side of the intramedullary nail 12 may be a side facing towards the outgoing side of the transverse bore 24 (e.g., towards a tip of the bone fastener 14 penetrating the transverse bore 24), whereas the lateral side may be a side facing towards the ingoing side of the transverse bore 24 (e.g., towards a head of the bone fastener 14). In many cases, the intramedullary nail 12 will be anatomically adapted so that the nail 12 inherently defines the medial and lateral sides, for example with respect to one or more its bending (e.g., as embodied by bent portion 22), an inclination of the transverse bore 24, and so on.

Returning to FIG. 5, the axial bore 32 and the internal thread 34 of the proximal portion 18 terminate at their lower ends in the transverse bore 24 of the proximal portion 18. In the present embodiment, the term "lower end" means that end which is nearer to the distal portion 20 of the intramedullary nail 12, and the term "upper end" is the opposite of the lower end.

The transverse bore 24 of the proximal portion 18 is formed as an angulated or oblique bore having a defined angle with respect to the longitudinal axis 30 of the proximal portion 18. Thus, the longitudinal axis 64 of the transverse bore 24 defines an angle with respect to the longitudinal axis 30 of the proximal portion 18.

Figure 6:
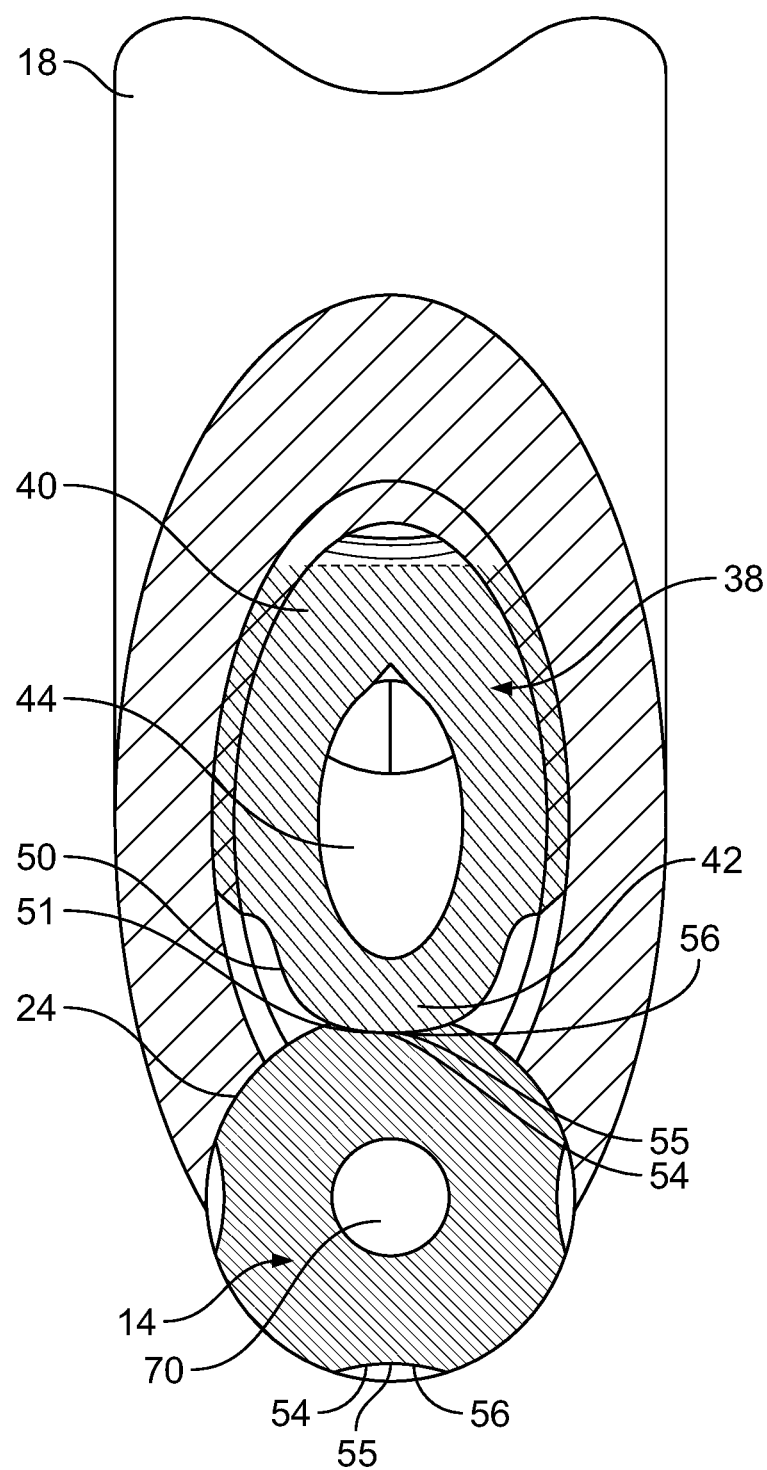
FIG. 6 is a detailed cross-sectional view along line A-A of the proximal portion of the implant system embodiment shown in FIG. 2.

FIG. 6 illustrates a detailed cross-sectional view along line A-A of the proximal portion 18 of the intramedullary nail 12 of the implant system embodiment 10 shown in FIG. 2. As shown in FIG. 6, the rounded edge 50 of the bone fastener engagement portion 42 of the coupling member 38 has a substantially rounded contact region 51. The rounded contact region 51 engages on a complementary rounded inner surface region 55 of one of the grooves 54 of the lag screw 14 as shown in FIG. 6. The rounded contact region 51 of the bone fastener engagement portion 42 and the rounded inner surface region 55 of the groove 54 define a substantially equal curvature.

As particularly illustrated in FIG. 6, the rounded edge 50 and the groove 54 substantially define complementary arc segments 51 and 55 in cross-section. That is, the rounded contact version 51 and the rounded inner surface region 55 are complementary formed to each other. The rounded contact region 51 of the coupling member 38 thus mates with the rounded inner surface region 55 of the groove 54 of the lag screw 14. Alternatively, the edge 50 of the coupling member 38 and/or the groove 54 of the lag screw 14 may have another shape in cross-section, e.g., a rectangular or triangular shape. These other shapes may be complementary to each other in similar manner. Thus, the grooves 54 of the lag screw 14 are of a size and shape that are complementary to the engagement part 50 of the bone fastener engagement portion 42 of the coupling member 38.

Due to the mating configuration of the rounded contact region 51 of the coupling member 38 and the rounded inner surface region 55 of the groove 54 of the lag screw 14, the coupling member 38 has an elongated contact region on the lag screw 14 instead of a single-point support. In other words, the rounded edge 50 of the coupling member 38 is engaged within one of the grooves 54 of the lag screw 14 in a substantially positive engagement fashion. Therefore, the mechanical forces provided by the coupling member 38 are not applied punctiformly on the lag screw 14, but instead distributed over an extended region of the lag screw 14, i.e., over the rounded inner surface 55 of the groove 54 along an arc segment.

Figure 7A:
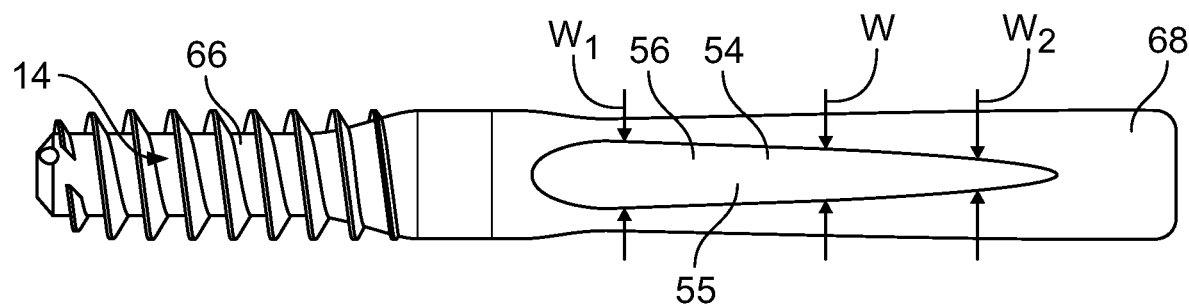
FIG. 7a shows a side view of a bone fastener embodiment.
Figure 7B:
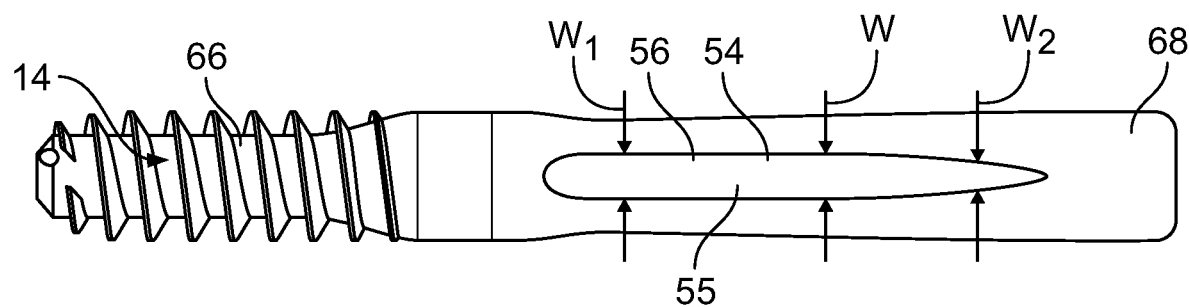
FIG. 7b shows a side view of an alternative embodiment of the bone fastener.

Referring to FIGS. 7a and 7b, there are shown a side view of a bone fastener embodiment 14 and of an alternative embodiment of the bone fastener 14. Both bone faster embodiments are formed as a lag screw 14.

As shown in FIGS. 7a and 7b, each of the embodiments of a lag screw 14 has a front portion 66 including a thread, for example a coarse thread, and a rear portion 68. The rear portion 68 is provided with a plurality of longitudinally extending grooves 54 (two are shown in FIGS. 2 and 3 and one is shown in FIGS. 7a and 7b) arranged on the peripheral surface of the rear shaft portion 68 along the axis of the lag screw 14. Typically, four grooves 54 are disposed on the peripheral surface of the lag screw 14 at intervals of 90° around the longitudinal axis of the lag screw 14. Each groove 54 defines a ramp 56 for engagement by the bone fastener engagement portion 42 of the coupling member 38. As shown in FIG. 3, each ramp 56 has a shallow end and a deeper end. The rising ramp 56 extends from the shallow end at a rear end of the rear portion 68 towards the threaded front portion 66 to the deeper end. The grooves 54 thus have an asymmetric depth profile. Further, each of the lag screws 14 shown in FIGS. 7a and 7b includes a central cannulation 70 (shown in FIG. 3) along the longitudinal axis of the lag screw 14. The rear portion 68 of the lag screw 14 may include at the rear end a co-axial bore and a recess (e.g., a hexalobular internal driving feature) for receiving a screw driver or a wrench (e.g., in the form of a entrained driving feature). Further, the at least one groove 54 of the lag screw 14 has a width w1 at the deeper end greater than a width w2 at the shallow end.

The difference between the lag screw embodiment 14 shown in FIG. 7a and that shown in FIG. 7b is that the width w of the at least one groove 54 of the lag screw 14 of FIG. 7a is continuously widening from the shallow end at the rear end of the rear portion 68 to the deeper end at the front end of the rear portion 68. Alternatively, the width w of the at least one groove 54 of the lag screw 14 of FIG. 7b widens from the shallow end into a portion with a constant width w towards the deeper end.

In an exemplary method for fracture fixation of bone using the above or other implant system embodiments, a guide wire is firstly inserted into a marrow cavity of bone. Then, the cannulated intramedullary nail 12 of the above or other embodiments is inserted over the guide wire into the marrow cavity of bone, i.e., is located in the intramedullary canal of a bone, e.g., the femur. The intramedullary nail 12 comprises the proximal portion 18, the transverse bore 24 and the coupling member 38 as generally described above. The guide wire is then removed. Then, a hole is bored transversally through the femur, the neck of the femur and into the head thereof for receiving a bone fastener 14. Then a bone fastener, e.g., a lag screw 14, is inserted through the transverse bore 24 of the intramedullary nail 12 into bone for stabilization of the bone fracture by operating a tool, e.g, a screw driver, such that one of the longitudinal grooves 54 of the lag screw 14 is aligned in the uppermost position. Finally, the coupling member 38 of the intramedullary nail 12 is driven for producing an engagement of the bone fastener engagement portion 42 with the bone fastener 14 penetrating the transverse bore 24 of the intramedullary nail 12, thereby preventing rotation of the bone fastener 14. In this case, the drive portion 40 of the coupling member 38, which is preassembled within the proximal portion 18 of the intramedullary nail 12, is turned downwards (i.e., in the direction of the longitudinal axis 30 of the proximal portion 18 towards the distal portion 20 of the intramedullary nail 12) with a screw driver until the bone fastener engagement portion 42, the rounded edge 50 thereof, respectively, is engaged within one of the grooves 54 of the lag screw 14.

Provided that the coupling member 38 is not completely tightened (i.e., the drive portion 40 of the coupling member 38 is not completely tightened), the lag screw 14 has the facility to slide within the transverse bore 24 only in a lateral direction (to the right in FIGS. 1 to 3) but is locked against rotation about its longitudinal axis. As the lag screw 14 is held against rotation by the coupling member 38 (i.e., by the rounded edge 50 of the bone fastener engagement portion 42), it merely slides through the transverse bore 24 and draws the head of the femur into close engagement with the rest of the bone. Due to the rising ramp 56 of the groove 54 of the lag screw 14, an uncontrolled medial sliding (to the left in FIGS. 1 to 3) of the lag screw 14 within the intramedullary nail 12 is prevented.

Since the proximal portion 18 of the intramedullary nail 12 and the coupling member 38 are configured as described above, the coupling member 38 can easily be preassembled or preloaded within the intramedullary nail 12, while allowing a simultaneous inserting/passage of a guide wire. The channel 46 of the intramedullary nail 12, the axial bore 32 of the proximal portion 18 of the intramedullary nail 12 and the through hole 44 of the coupling member 38 (which together define a cannulation) may be substantially aligned to permit insertion of a guide wire completely through the preassembled coupling member 38 and the intramedullary nail 12. Thus, a guide wire can be used to guide the intramedullary nail 12, including the preassembled coupling member 38, into the intramedullary canal of, e.g., the femur. Therefore, the coupling member 38 has not to be assembled intraoperatively. Consequently, the operation steps that need to be performed by a surgeon are reduced, whereby the surgical procedure and the implantation of the intramedullary nail 12 within an intramedullary canal of a femur is facilitated and simplified. Due to this fact, the operation time is reduced. Since the intramedullary nail 12 is provided with the coupling member (including the bone fastener engagement portion 42 and the drive portion 40 non-rotatably connected thereto) that is preassembled into the axial bore 32 of the proximal portion 18 of the intramedullary nail 12, the amount of time associated with implanting the intramedullary nail 12 as well as the number of parts which have to be handled by a surgeon is reduced.

While the coupling member and its drive portion and bone fastener engagement portion as described herein are substantially formed as a short bold having a rounded edge, the coupling member and its drive portion and/or bone fastener engagement portion can be adapted to different applications as needed (e.g., in terms of shape, length, width, thickness, etc.) for use in the intramedullary nail 12 of the implant system 10 shown in FIGS. 1 to 3.

All parts of the implant system described above are easily and cheaply produceable with the current state of machine tools. Since the guide wires deviate to an eccentric position (e.g., to the medial side) within the intramedullary nail due to the bending of the intramedullary nail, the eccentric engagement of the bone fastener engagement portion of the coupling member facilitates the fence of the guide wire inside the intramedullary nail.

While the rod-shaped body of the intramedullary nail includes a distal portion and a bent portion in the embodiment illustrated in the drawings, the nail body can be adapted as needed (e.g., in terms of shape, length, width, thickness, etc.) for use in orthopaedic surgery for fixation of bone and for insertion into an intramedullary canal of, e.g., a femur. Thus, the intramedullary nail can be adapted to different applications and may thus have a different shape. Moreover, while the threads as shown herein are one start threads, they could also be multiple start threads (e.g., a two-start thread).

While the bone fastener as described herein is formed as a lag screw, the bone fastener can be of any type of, e.g., a femoral neck screw or any kind of blade, and can be adapted to different applications as needed. The bone fasteners may thus have different diameters, lengths, shapes or threads. Further, the bone fastener, the implant and/or the coupling member or parts thereof as described above can generally be made of stainless steel, titanium or any other biocompatible material.

While the above embodiments have exemplarily been described in relation to a bone screw and an intramedullary nail, it will be readily apparent that the techniques presented herein can also be implemented in combination with other types of bone fasteners (such as bone pegs having a rod-like or pin-like shafts, wire-like bone fasteners such as Kirschner wires, etc.) as well as other types of implants (such as bone plates, bone distractors, etc). Accordingly, the present disclosure is not limited to any type of bone fastener or any type of implant.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implant system for fixation of a long bone, comprising:
    an intramedullary nail having an axial bore and a transverse bore intersecting the axial bore, the axial bore having a threaded inner surface and defining a first axis, the transverse bore defining a second axis oriented at an oblique angle relative to the first axis;
    a lag screw having a longitudinally extending groove formed in an exterior thereof; and
    a coupling member having a drive portion, an engagement portion, and a through hole extending through the drive portion and engagement portion, the through hole defining a third axis, the drive portion having a threaded outer surface configured to engage the threaded inner surface of the axial bore, the engagement portion extending from and integrally formed with the drive portion, the engagement portion having an outer surface of revolution, a planar end surface, and an edge extending therebetween, the planar end surface defining a plane perpendicular to the third axis, wherein the edge of the coupling member is configured to engage the groove to prohibit rotation of the lag screw when the lag screw is disposed within the transverse bore and the coupling member is disposed in the axial bore,
    wherein the third axis lies in a proximal-distal plane, the proximal-distal plane bisecting the coupling member so that the edge of the engagement portion is divided into a first portion at one side of the proximal-distal plane and a second portion at another side of the proximal-distal plane, the engagement portion and groove being dimensioned such that only the first portion can be received within the groove.

2. The system of claim 1, wherein the groove of the lag screw includes a ramped surface.

3. The system of claim 1, wherein the edge defines a first arc segment.

4. The system of claim 3, wherein the groove defines a second arc segment, the first and second arc segments being complementary to each other.

5. The system of claim 1, wherein the outer surface of revolution is cylindrical, and the edge defines an extended contact region between the outer surface of revolution and the planar end surface.

6. The system of claim 5, wherein the extended contact region is curved in at least one plane.

7. The system of claim 5, wherein a diameter of the cylindrical outer surface is larger than a diameter of the planar end surface.

8. The system of claim 1, wherein the drive portion and engagement portion each have the length, the length of the drive portion being greater than a length of the engagement portion.

9. The system of claim 1, wherein the intramedullary nail includes a proximal portion, a distal portion, an intermediate portion, and a channel, the axial bore being disposed in the proximal portion, and the channel extending through the intermediate and distal portions and communicating with the axial bore.

10. The system of claim 1, wherein the groove is defined by an inner surface region of the lag screw, the inner surface region and the edge having substantially equal curvatures.

11. An implant system for fixation of a long bone, comprising:
an intramedullary nail having an axial bore and a transverse bore, the transverse bore intersecting the axial bore at an oblique angle;
a lag screw having an inner surface region defining a longitudinally extending groove; and
a coupling member having a drive portion, an engagement portion, and a through hole extending through the drive portion and engagement portion, the through hole defining a longitudinal axis of the coupling member, the engagement portion extending from and integrally formed with the drive portion, the engagement portion having a cylindrical outer surface, a planar end surface, and an edge extending therebetween, the planar end surface defining a plane perpendicular to the longitudinal axis of the coupling member,
wherein the coupling member is axially moveable within the axial bore via the drive portion so that a portion of the edge of the engagement portion is brought into contact with the inner surface region of the lag screw when disposed within the transverse bore in order to prevent rotation of the lag screw,
wherein the longitudinal axis of the coupling member axis lies in a proximal-distal plane, the proximal-distal plane bisecting the coupling member so that the edge of the engagement portion is divided into a first portion at one side of the proximal-distal plane and a second portion at another side of the proximal-distal plane, the engagement portion and groove being dimensioned such that only the first portion can be received within the groove.

12. The system of claim 11, wherein the edge is curved in at least one plane.

13. The system of claim 11, wherein the edge is curved in at least two planes.

14. The system of claim 11, wherein the edge and inner surface region define complementary arc segments in cross-section.

15. The system of claim 14, wherein contact between the edge and inner surface region forms a contact region having a two-dimensional extension.

16. An implant system for fixation of a long bone, comprising:
an intramedullary nail having an axial bore and a transverse bore intersecting the axial bore,
the axial bore having a threaded inner surface and defining a first bore axis, the transverse bore defining a second bore axis oriented at an oblique angle relative to the first bore axis;
a lag screw having a longitudinally extending groove formed in an exterior thereof; and
a set screw disposed in the axial bore and having a threaded portion, an unthreaded portion, and a through hole extending through the threaded and unthreaded portions, the through hole defining a longitudinal axis of the set screw, the threaded portion being configured to engage the threaded inner surface of the axial bore, the unthreaded portion having an outer surface of revolution, a planar end surface, and an edge extending therebetween, the planar end surface defining a plane perpendicular to the longitudinal axis of the set screw,
wherein, when the lag screw is received within the transverse bore, the set screw is configured to eccentrically engage the lag screw such that a portion of the edge is received within the groove to prohibit rotation of the lag screw,
wherein the longitudinal axis of the set screw lies in a proximal-distal plane, the proximal-distal plane bisecting the coupling member so that the edge of the engagement portion is divided into a first portion at one side of the proximal-distal plane and a second portion at another side of the proximal-distal plane, the engagement portion and groove being dimensioned such that only the first portion can be received within the groove.

17. The system of claim 16, wherein the lag screw is configured to be received within the transverse bore so that a screw axis thereof is coaxial with the second bore axis, and the set screw is configured to be received within the axial bore so that the longitudinal axis thereof is coaxial with the first bore axis.

18. The system of claim 16, wherein the outer surface of revolution is cylindrical and has a first diameter, the drive portion has a second diameter, and the planar end surface has a third diameter, the first, second and third diameters each differing from one another.

19. The system of claim 16, wherein the drive portion has a planar end surface and a tool receiving portion extending through the planar end surface of the drive portion.

* * * * *